(12) United States Patent
Ranta et al.

(10) Patent No.: US 9,233,179 B2
(45) Date of Patent: Jan. 12, 2016

(54) TOUCHSCREEN SANITIZING SYSTEM

(71) Applicant: Vioguard LLC, Kirkland, WA (US)

(72) Inventors: Craig Ranta, Redmond, WA (US);
Steven Swedenberg, Kirkland, WA (US)

(73) Assignee: VIOGUARD LLC, Kirkland, WA (US)

( * ) Notice: Subject to any disclaimer, the term of this patent is extended or adjusted under 35 U.S.C. 154(b) by 0 days.

(21) Appl. No.: 14/504,275

(22) Filed: Oct. 1, 2014

(65) Prior Publication Data

US 2015/0182647 A1 Jul. 2, 2015

Related U.S. Application Data

(60) Provisional application No. 61/885,408, filed on Oct. 1, 2013.

(51) Int. Cl.
*A61L 2/10* (2006.01)
*G06F 3/041* (2006.01)
*G06F 3/0488* (2013.01)
*G01J 5/00* (2006.01)
*A61L 2/24* (2006.01)

(52) U.S. Cl.
CPC .............. *A61L 2/10* (2013.01); *G01J 5/0022* (2013.01); *G06F 3/0412* (2013.01); *G06F 3/0488* (2013.01); *A61L 2/24* (2013.01); *A61L 2202/14* (2013.01)

(58) Field of Classification Search
CPC ........... A61L 2/10; A61L 2/24; G01J 5/0022; G06F 3/0412
See application file for complete search history.

(56) References Cited

U.S. PATENT DOCUMENTS

| | | |
|---|---|---|
| 8,431,910 B1 | 4/2013 | Perry |
| 2006/0188389 A1 | 8/2006 | Levy |
| 2009/0252646 A1* | 10/2009 | Holden et al. ................. 422/24 |
| 2011/0256019 A1 | 10/2011 | Gruen et al. |
| 2012/0019488 A1* | 1/2012 | McCarthy ..................... 345/179 |

FOREIGN PATENT DOCUMENTS

WO 2013081672 6/2013

* cited by examiner

*Primary Examiner* — Mark R Gaworecki
(74) *Attorney, Agent, or Firm* — Lowe Graham Jones, PLLC

(57) ABSTRACT

A sanitizing system for use with monitors, particularly including touchscreen monitors, includes an ultraviolet light source positioned about a periphery of the monitor and configured to transmit light toward the monitor. A sensor detects the presence of an object such as a human finger in the close vicinity or in contact with the monitor in order to stop the operation of the lights.

15 Claims, 4 Drawing Sheets

TOUCHSCREEN SANITIZING SYSTEM

PRIORITY CLAIM

This application claims the benefit of U.S. Provisional Application No. 61/885,408 filed Oct. 1, 2013, the contents of which are incorporated by reference.

FIELD OF THE INVENTION

The present invention relates to systems and methods for sanitizing monitors, particularly including monitors configured with a touch-screen input.

BACKGROUND OF THE INVENTION

Widespread use of shared touchscreen displays is common in retail and healthcare applications. These touchscreens are cleaned infrequently and consequently can harbor infectious pathogens, which are transmitted from person to person when they use the touchscreen. Frequent cleaning is impractical and cannot be performed often enough to keep the contamination levels in check.

SUMMARY OF THE INVENTION

The present invention relates to a sanitizing system for use with monitors, particularly including touchscreen monitors. In a preferred version of the invention, a monitor includes an ultraviolet light source positioned about a periphery of the monitor and configured to transmit light toward the monitor. One or more such UV sources may be used, to ensure complete coverage of the monitor and to provide a desired intensity of light shining toward the monitor.

In some versions of the invention, a motion sensor or proximity sensor is provided in order to detect the presence of an object such as a human finger in the close vicinity of the monitor or actually touching the monitor screen. In one example, the sensor is in the form of an infrared light transmitter and receiver positioned on opposite sides of the monitor to detect an object in the path between the transmitter and receiver.

In other versions, the sensor may monitor different parameters such as heat or optical changes in the region of the monitor that would indicate the presence of a person touching the surface of the screen.

In yet other versions, the sensor is the touchscreen itself, with programming instructions responding to the initial touch detected by the touchscreen and operating an appropriate UV light sanitizing cycle in response to the detected touch.

BRIEF DESCRIPTION OF THE DRAWINGS

Preferred and alternative examples of the present invention are described in detail below with reference to the following drawings.

DETAILED DESCRIPTION OF THE PREFERRED EMBODIMENT

Figure 1:
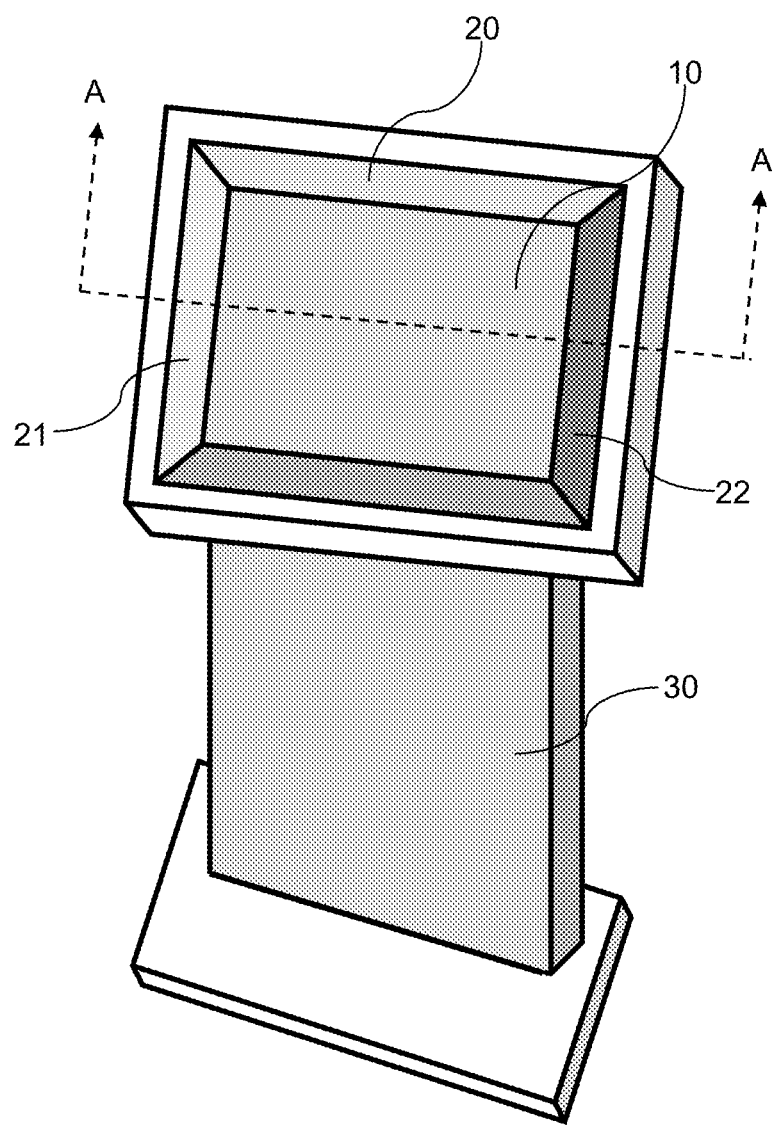
FIG. 1 is a perspective view of a representative touchscreen monitor having a sanitizing system, shown on a representative stand or kiosk.

A preferred touchscreen sanitizing system is incorporated into a system having a touchscreen monitor which, in a typical use, is placed in a location for use by the general public or by many people. With reference to FIG. 1, a stand or kiosk 30 may be configured to support a touchscreen monitor 10 that is attached to the kiosk. Most preferably, the screen is surrounded by a bezel 20, including left and right bezel sides 21, 22. In some implementations, the monitor may be recessed below a surrounding frame or housing, and therefore may not have a snugly surrounding bezel as with the preferred and illustrated version.

Figure 2:
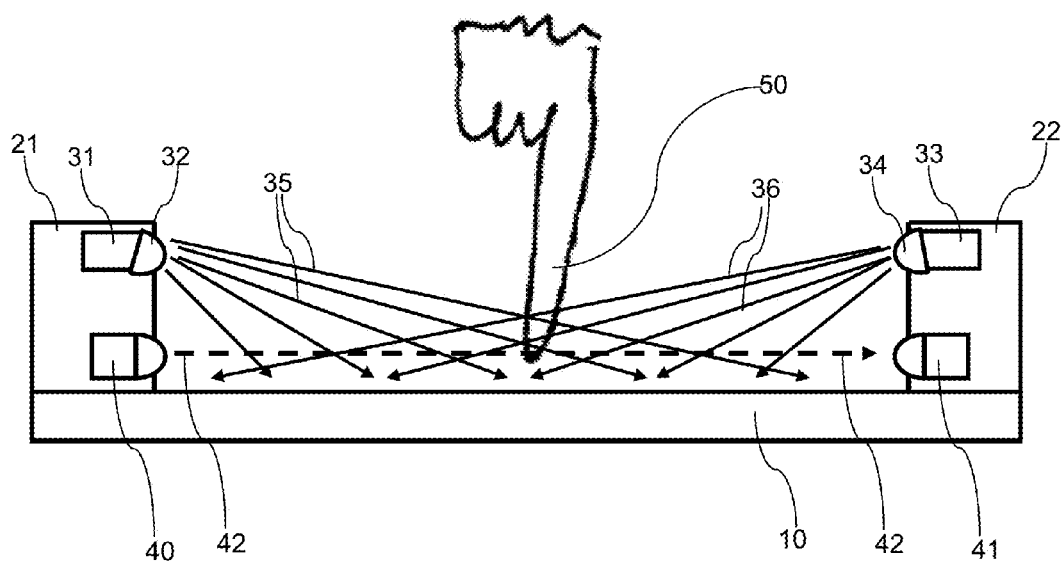
FIG. 2 is a sectional view of the monitor and sanitizing system of FIG. 1, as viewed along plane A-A from FIG. 1.

As best seen in FIG. 1, and the sectional view of FIG. 2, the preferred version of the invention is one in which the monitor 10 includes a shallow bezel 20, either attached to an existing touchscreen or built into the existing touchscreen. The touchscreen 10 may be configured as an LCD, LED, or any other form of display configured to present images and information and also to detect contact on the screen associated with those images.

The bezel 20 houses one or more UVC lamps, preferably configured to be extremely thin and long UVC fluorescent lamps of 3-5 mm in thickness. As illustrated in FIG. 2, each of the left side bezel 21 and right side bezel 22 includes a UVC light source 31, 33 configured to produce UVC light that may be directed through an optional associated lens 32, 34 to orient the light toward the surface of the touchscreen monitor 10.

The lamps are positioned so that there is no direct illumination from the lamp to the user's eyes, as UVC can be harmful to the eyes. The positioning is most preferably within the bezel 20 or a form of shield that blocks the light from direct transmission to the eyes of a user. In the illustrated example, the UVC sources and accompanying lenses are recessed beneath the bezel sides 21, 22 in order to shield the light from being directed toward the eyes.

In one version of the invention, a long, rod-shaped optic lens transmissive to 254 nm light is placed in front of each lamp to focus the light in a sheet across the touchscreen surface. Thus, the illustration of FIG. 2 is a sectional view taken through the rod-shaped lenses 32, 34, which may extend along each of the two bezel sides 21, 22 substantially along the entire length between the top and bottom of the bezel. There may be two lamp/lens pairs (31, 32 and 33, 34) as in the illustrated version, and they may be placed on the long axis of the display at the top and bottom, at the left and right, or along all four sides.

The UVC lamps are configured to illuminate the touch screen during periods of inactivity. While the touchscreen is not being used, a continuous low level of UVC light illuminates the touchscreen surface to kill pathogens.

The intensity of the UVC light is designed to kill pathogens at a rate greater than which they are deposited on the touchscreen, ensuring a continuously low level which reaches zero after a period of time. Although a frequently used touchscreen will still have some pathogens immediately after being touched, lower concentrations of pathogens result in a lower chance of infectious disease transfer than higher levels of pathogens.

Since UVC light can also be harmful to the skin, preferred examples of the invention include a controller or other component to cease illumination of the screen when the touch screen is in use. One version incorporates an infrared sensor to detect use of the screen, as shown in the example of FIG. 2. As illustrated, one or more IR light transmitters 40 is placed on one side of the touchscreen (such as on a first side 21 of the bezel) and one or more IR light receivers 41 is placed on the opposite side of the touchscreen (such as on the second opposite side 22 of the bezel). In this version, when a finger 50 or any other object breaks the plane of the IR light 42 (and therefore touches the screen or is in the vicinity of the UVC light), the UVC lamps are turned off. In the illustrated example, an array of infrared sources and sensors is focused to form an invisible grid that senses the presence of a finger. When an object such as a finger breaks the path between a sensor and a source of IR light, the system shuts down the UVC lamps immediately. The lamps remain off thereafter during touchscreen activity. After a period of inactivity, a timer expires and turns the lamps back on.

In another version, the microprocessor associated with the touch screen detects contact of an object (such as a finger) with the screen, and in response to screen contact the controller issues a command to turn off the light. After a period of inactivity, a timer causes the UVC lamps to turn back on. This version would preferably not include an IR sensor, and instead would rely on the sensors already incorporated into a touch screen. In some versions the IR sensor may be preferable because it could more readily be incorporated into an existing system.

Yet other versions of the invention may incorporate motion sensors or other forms of contact or proximity sensors to detect a user's finger coming into contact with, or close proximity to, the screen. Such sensors may detect changes in heat or light in the vicinity of the screen. As another example, a light sensor may detect the presence of a person in close proximity with the screen, even without the person's hand yet moving toward the screen. In such a version, the processor may cease illumination of the UVC lamp after a detection of such presence (as a function of a lower detected light level), and resume illumination after the detected light level has returned to an expected background level indicating no one is present.

In the illustrated version, the IR detector is shown as being relatively closer to the display than the UVC lamp, positioned between the UVC lamp and the display. In other versions the IR light and detector may be reversed with respect to the UVC lamp, such that the UVC lamp is positioned between the display surface and the IR detector.

Figure 3:
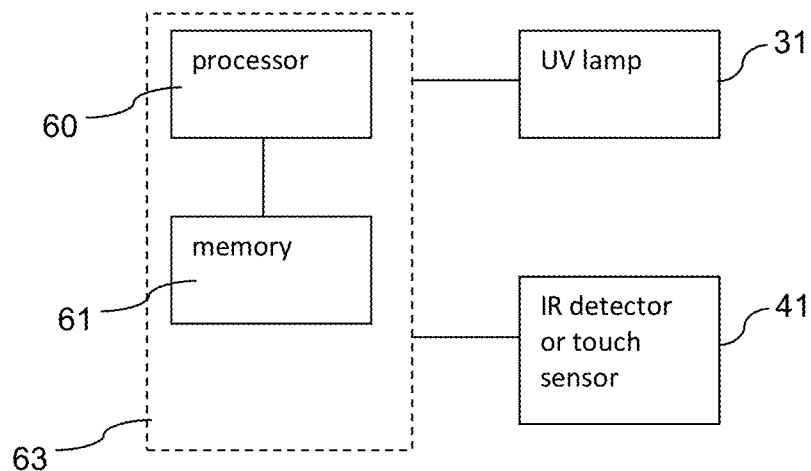
FIG. 3 is a block diagram of a preferred implementation of a touchscreen monitor sanitizing system.
Figure 4:
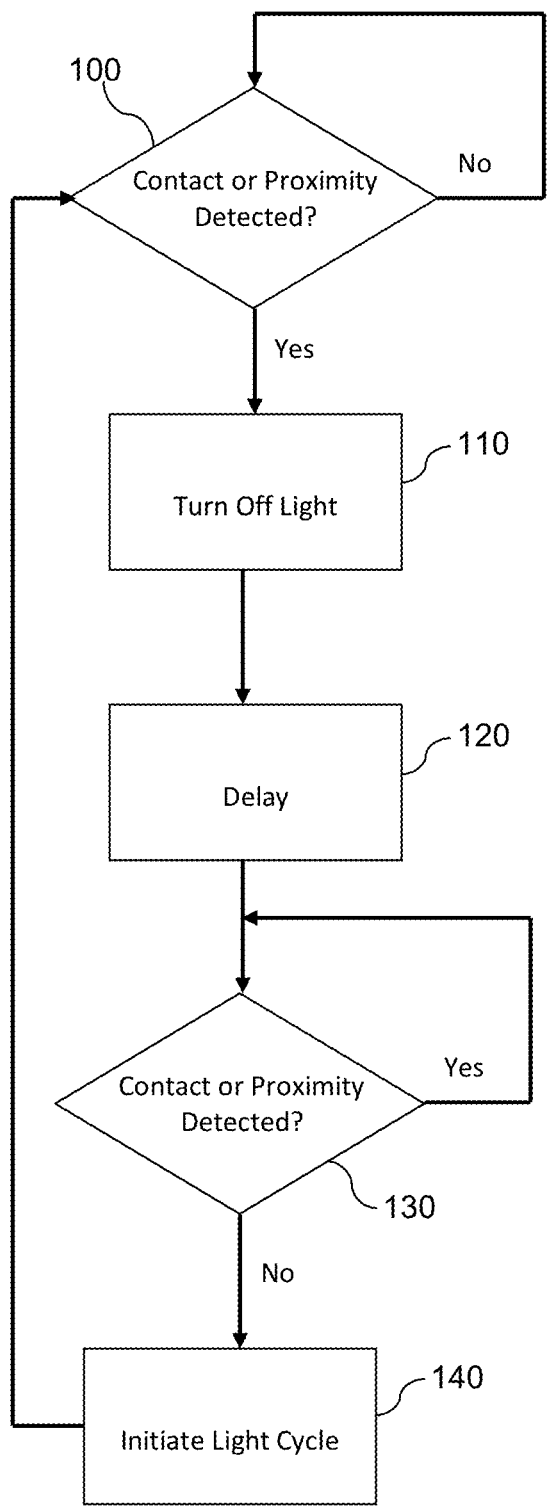
FIG. 4 is a flow diagram of a preferred touchscreen monitor sanitizing method.

The timer and UVC lamp controller 63 is preferentially implemented in a microprocessor 60, such as shown in FIG. 3, following a process as illustrated in the flow diagram of FIG. 4, in which a memory 60 associated with the processor 60 contains stored programming instructions enabling the processor to implement the steps of the flow diagram. The processor is preferably in communication with the UV lamps (e.g., 31) to control the operation of the lamps, and likewise in communication with the sensor such as the IR detector 41 or the other heat, light, or other proximity or touch sensors as described above.

Initially, the UVC light sources are illuminated and remain in the illuminated state as described above while no contact or proximity is detected. At a first block 100, the processor 60 evaluates whether the sensor (such as the IR receiver 41) has detected the presence of an object such as a finger close to the touchscreen. So long as there are no objects close to or touching the screen, the system remains in this continued state of illuminating the UVC light and monitoring for contact.

In one version, once contact is detected, the process proceeds to a next block 110 in which the processor turns off the UVC light. With the light turned off, in the preferred version the process proceeds to a next block 120 to implement a delay before turning the light back on again. In one example, a timer, such as operated by the programming instructions, begins a count for 60 seconds each time a proximity or contact is detected, counting down (or up) for as long as there is no contact or proximity thereafter. Each contact or proximity begins a fresh count.

Once the count is completed, the processor directs the UVC lamps to illuminate again as long as there is no contact. Thus, after the delay cycle 120 has completed, the process queries whether there is contact or proximity detected at a next block 130. If there is no such contact or proximity, the process proceeds to a next block 140 in which the UVC light sources are illuminated again. Thereafter, the process continues to monitor for contact by returning to the original block 100 to monitor for contact.

Other enhancements to the touchscreen sanitizer include a UVC sensor to measure UV output and detect a faulty bulb, giving a failure indication such as an audible alarm or the illumination of an LED or other visual indicator.

While the preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined entirely by reference to the claims that follow.

The embodiments of the invention in which an exclusive property or privilege is claimed are defined as follows:

1. A system for sanitizing a touchscreen monitor, comprising:
an ultraviolet light source positioned about a periphery of the touchscreen monitor and configured to direct light toward the surface of the touchscreen monitor;
a sensor configured to detect the presence of an object in close proximity to the touchscreen monitor;
a shield positioned about the periphery of the touchscreen monitor and configured to block the transmission of light emitted from the ultraviolet light source in a direction away from the touchscreen monitor;
a lens positioned between the ultraviolet light source and the touchscreen monitor, the lens being configured to focus the ultraviolet light onto the touchscreen monitor; and
a controller in communication with the ultraviolet light source and the sensor, the controller being configured to automatically stop the illumination of the ultraviolet light source in response to the detected presence of an object by the sensor, the controller further being configured to automatically cause the ultraviolet light source to resume illumination after the object is no longer detected by the sensor.

2. The system of claim 1, wherein the shield comprises a bezel for the touchscreen monitor.

3. The system of claim 1, wherein the sensor comprises an infrared transmitter and an infrared receiver, the infrared transmitter and the infrared receiver being positioned on opposite sides of the touchscreen monitor.

4. The system of claim 1, wherein the sensor comprises the touchscreen monitor.

5. The system of claim 1, wherein the sensor comprises a motion sensor.

6. The system of claim 1, wherein the controller is further configured to automatically cause the ultraviolet light source to resume illumination after a period of delay after the object is no longer detected by the sensor.

7. The system of claim 1, wherein the sensor is positioned between the ultraviolet light source and the touchscreen monitor.

8. The system of claim 1, wherein the ultraviolet light source is positioned between the sensor and the touchscreen monitor.

9. The system of claim 1, wherein the ultraviolet light source is positioned on opposing sides of the touchscreen monitor.

10. The system of claim 9, wherein the ultraviolet light source comprises a pair of fluorescent UVC bulbs placed on opposing sides of the touchscreen monitor.

11. The system of claim 1, wherein ultraviolet light source comprises a fluorescent UVC bulb and the lens comprises a rod-shaped optic lens.

12. The system of claim 1, wherein controller further comprises a microprocessor and a memory, the memory containing stored programming instructions operable by the memory to cause the ultraviolet light source to illuminate and stop illumination in response to input from the sensor.

13. A system for sanitizing a touchscreen monitor, comprising:
   an ultraviolet light source positioned about a periphery of the touchscreen monitor and configured to direct light toward the surface of the touchscreen monitor;
   a sensor configured to detect the presence of an object in close proximity to the touchscreen monitor;
   a lens positioned between the ultraviolet light source and the touchscreen monitor, the lens being configured to focus the ultraviolet light onto the touchscreen monitor; and
   a controller in communication with the ultraviolet light source and the sensor, the controller being configured to automatically stop the illumination of the ultraviolet light source in response to the detected presence of an object by the sensor, the controller further being configured to automatically cause the ultraviolet light source to resume illumination after the object is no longer detected by the sensor.

14. The system of claim 13, wherein the ultraviolet light source comprises a fluorescent UVC bulb.

15. The system of claim 13, wherein the lens comprises a rod-shaped optic lens.

* * * * *